United States Patent [19]

Dilts et al.

[11] Patent Number: 5,016,213
[45] Date of Patent: May 14, 1991

[54] METHOD AND APPARATUS FOR CONTROLLING AN ELECTRICAL DEVICE USING ELECTRODERMAL RESPONSE

[76] Inventors: Robert B. Dilts, 3543 La Madrona Dr., Scotts Valley, Calif. 95066; Trone L. Miller, 1960 California St., #17, Mountain View, Calif. 94040

[21] Appl. No.: 642,318

[22] Filed: Aug. 20, 1984

[51] Int. Cl.$^5$ ............ G06F 1/00; G06F 15/28
[52] U.S. Cl. ............ 364/900; 364/410; 364/916.5
[58] Field of Search ............ 364/410, 413, 415, 417, 364/200 MS File, 900 MS File, 413.01–413.06, 413.27; 324/62 R, 63, 65 R; 128/630, 734, 902, 905; 273/1 GC, 85 G, 148 B

[56] References Cited

U.S. PATENT DOCUMENTS

| | | | |
|---|---|---|---|
| 2,339,579 | 1/1944 | Milne et al. | 128/2.1 |
| 3,556,083 | 1/1971 | Grichnik et al. | 128/2.1 |
| 3,727,604 | 4/1973 | Sidwell et al. | 128/2.1 Z |
| 3,772,593 | 11/1973 | Sidhu | 324/62 R |
| 3,841,316 | 10/1974 | Meyer | 128/734 X |
| 3,870,034 | 3/1975 | James | 128/905 X |
| 4,088,125 | 5/1978 | Forgione et al. | 128/734 X |
| 4,149,716 | 4/1979 | Scudder | 273/85 G X |
| 4,358,118 | 11/1982 | Plapp | 273/85 G |
| 4,461,301 | 7/1984 | Ochs | 128/630 |

Primary Examiner—Gary V. Harkcom
Assistant Examiner—John A. Merecki
Attorney, Agent, or Firm—Thomas M. Freiburger

[57] ABSTRACT

A method and apparatus utilizing electrodermal response as a control mechanism. A specific embodiment of the method and apparatus utilizing a personal computer having a game paddle input port is described. The time rate of change in the electrodermal response of a biologic individual is sensed independently of the absolute value of the electrodermal response and continuously adjusted toward a time rate of change approaching the average time rate of change which the biologic individual cna consciously achieve in such electrodermal response. The resultant time rate of change is utilized as the input to a computer in order to provide the control.

6 Claims, 3 Drawing Sheets

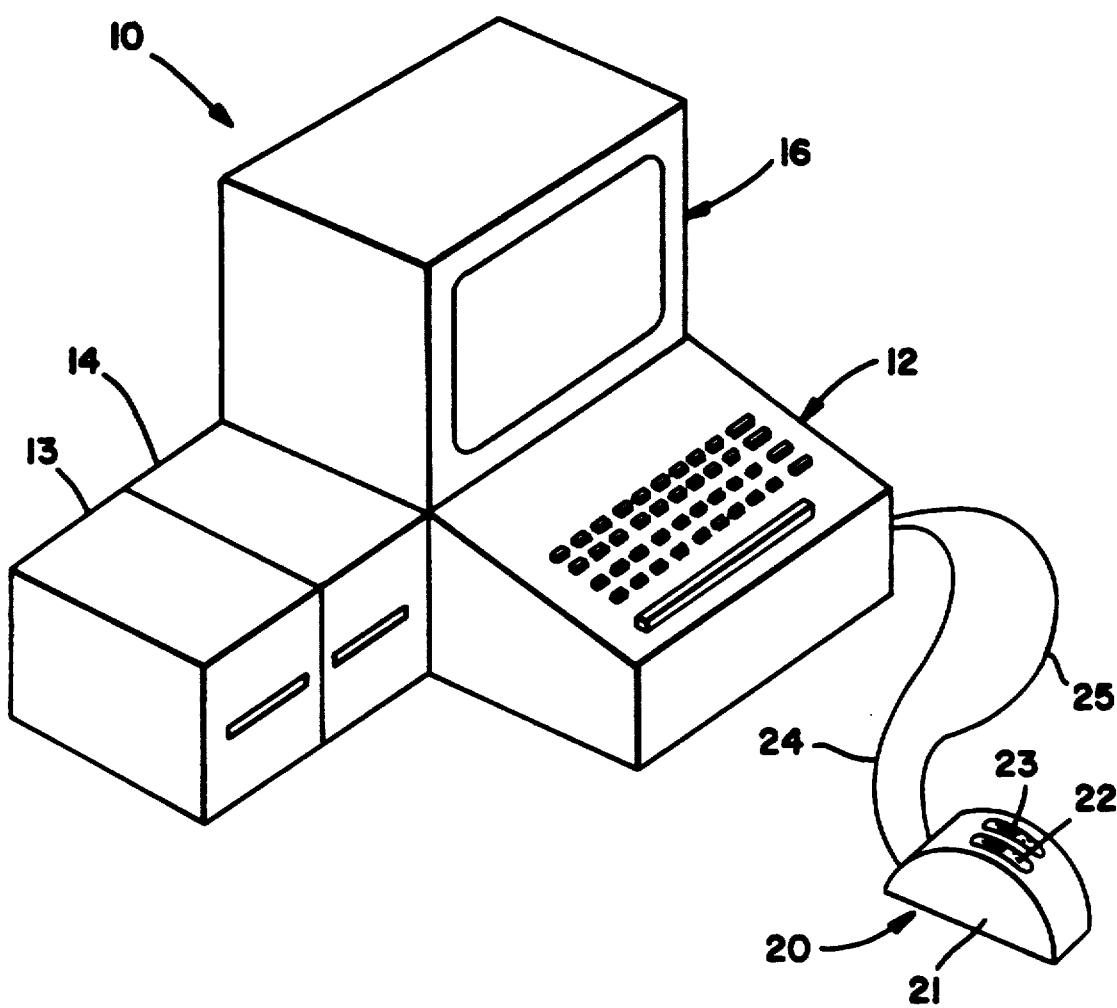
FIG _ 1
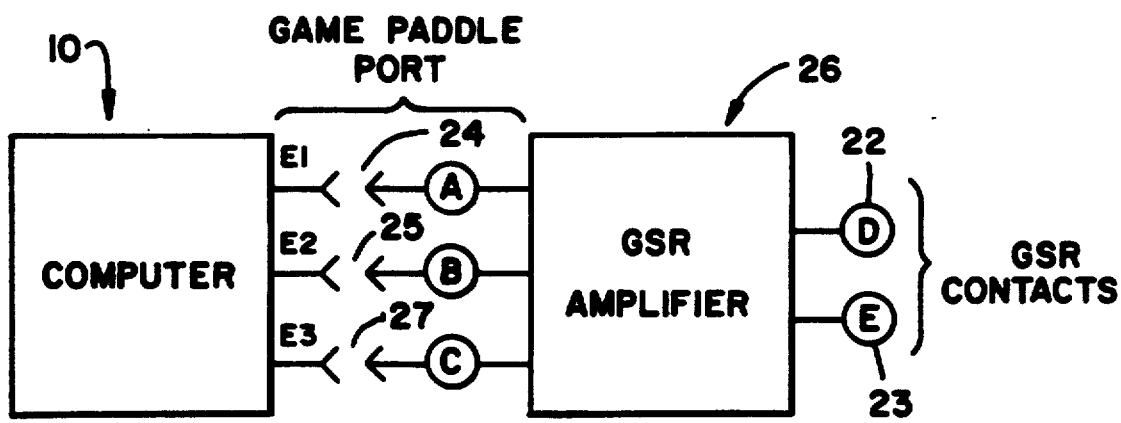
FIG _ 2

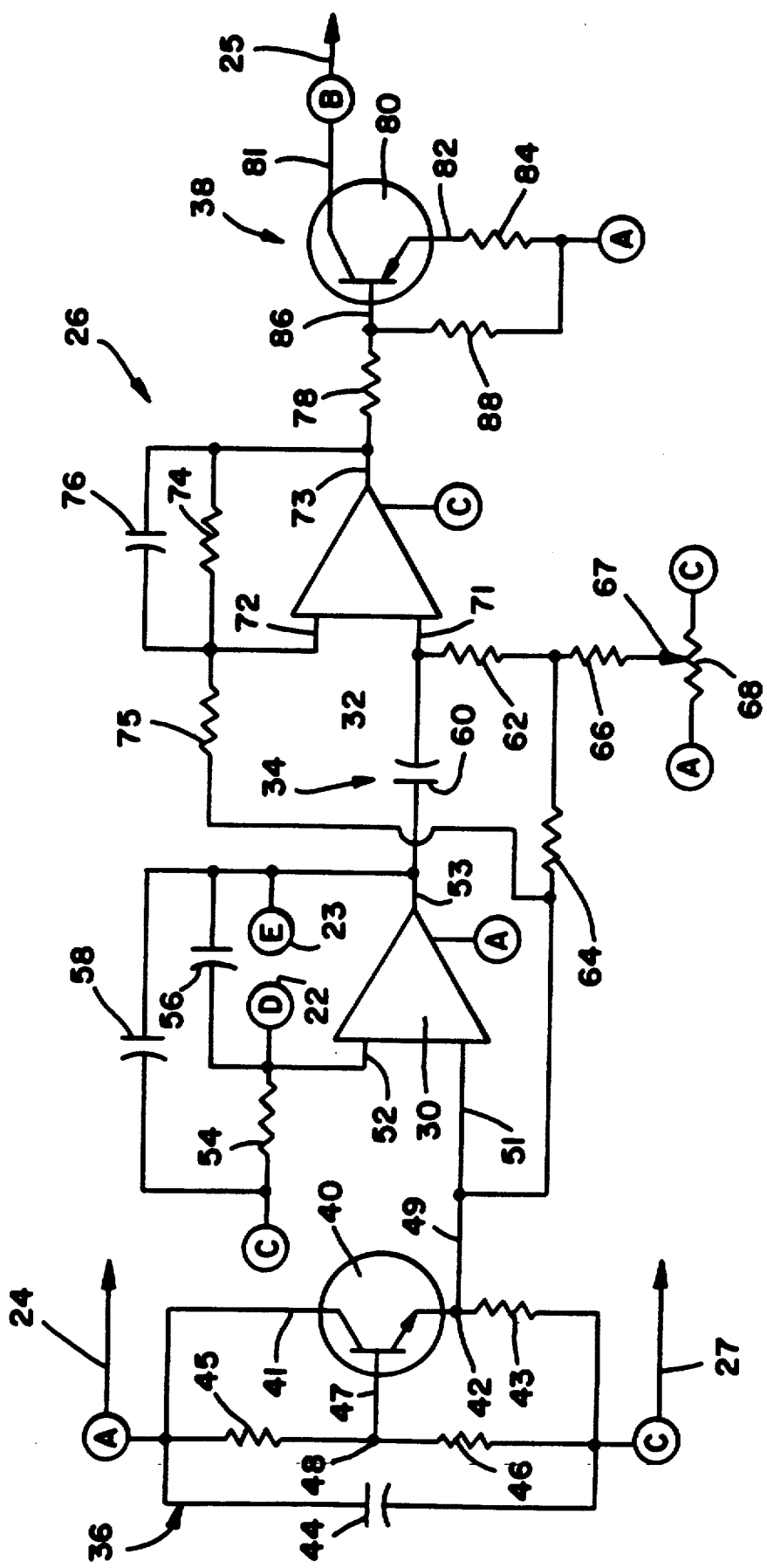
FIG_3

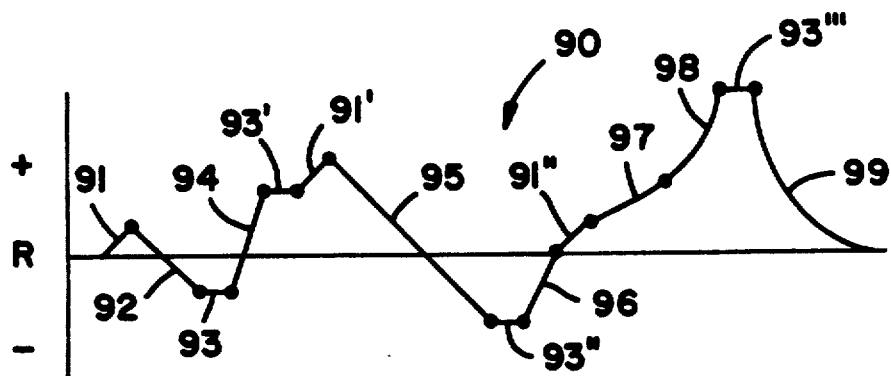
FIG_4
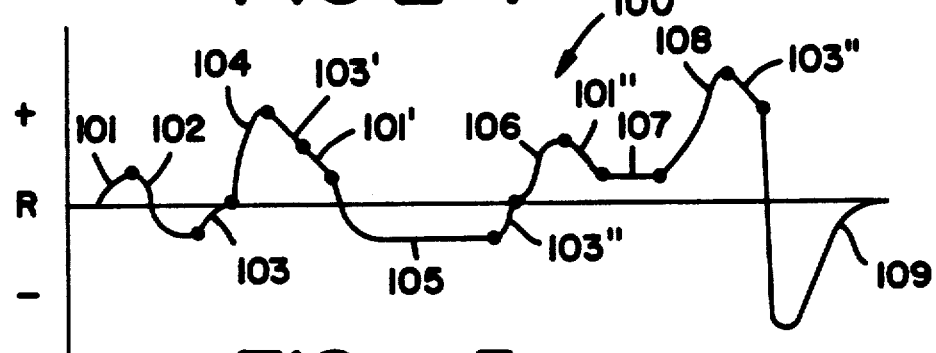
FIG_5
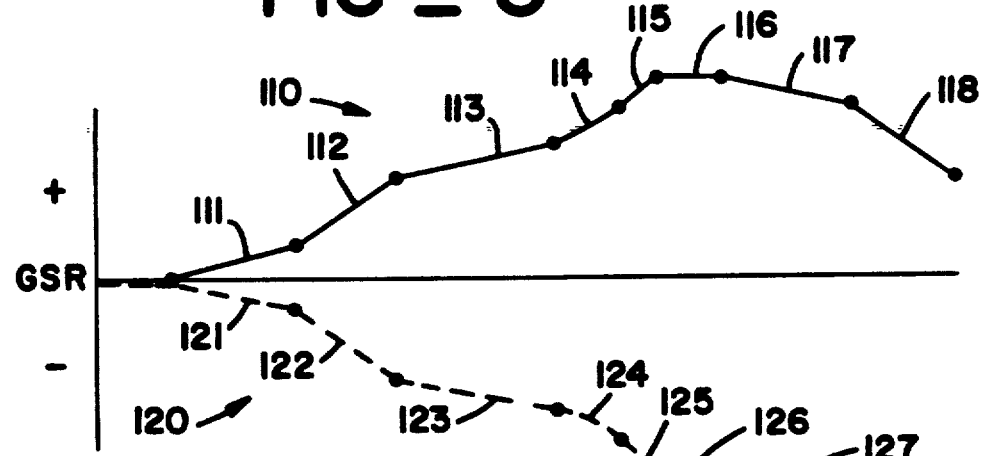
FIG_6
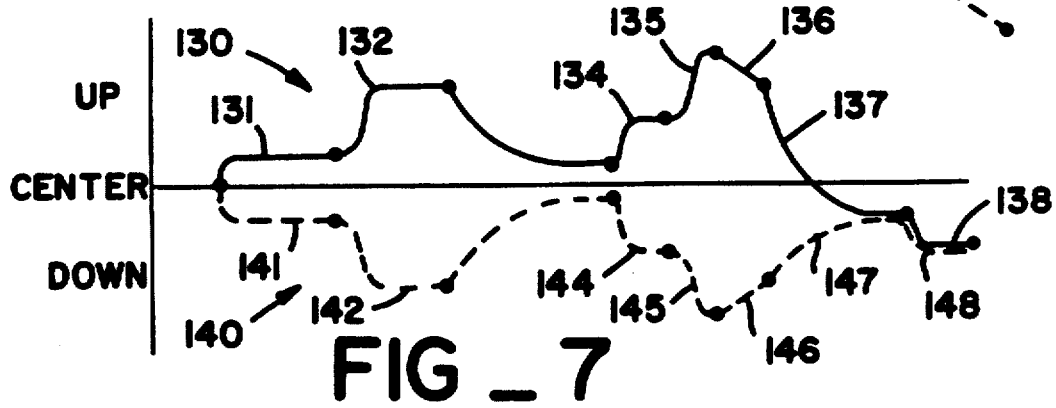
FIG_7

METHOD AND APPARATUS FOR CONTROLLING AN ELECTRICAL DEVICE USING ELECTRODERMAL RESPONSE

FIELD OF THE INVENTION

This invention relates to methods of and apparatus for sensing responses in autonomic systems of biologic individuals and more particularly to a method and apparatus utilizing electrodermal response in biologic individuals as a control means.

BACKGROUND OF THE INVENTION

All living individuals, i.e., plants and animals, are known to have complex systems for automatically maintaining their biological balances substantially independently of their central nervous system. Such systems are called "autonomic systems" and in warm blooded animals, for example, such systems are known to control such things as the body temperature, respiration rate and heart beat of the animal, for purposes which are fairly well understood. However, both plants and animals have been found to have autonomic systems controlling their electrodermal response for purposes which are not fully understood.

Furthermore, it has been found that the central nervous system of human beings can consciously and subconsciously control their autonomic systems including their electrodermal response. The conscious and subconscious control of respiration rate by the central nervous system is a common experience of all mankind. In recent years bio-feedback devices have enabled human experience of the conscious and subconscious control of such autonomic systems as heart beat, blood pressure, temperature, and electrodermal response, for example.

However, the conscious and subconscious control of such autonomic systems by the central nervous system as experienced in the prior art is often erratic, at best, particularly for electrodermal control. This is due, in part, to the fact that such autonomic systems are subject to simultaneous autonomic control which is by nature a primary effect, whereas the conscious and subconscious control of such autonomic systems by the central nervous system is a secondary effect. In other words, although a human being may be able to consciously achieve an electrodermal response through the central nervous system, such response will tend to stimulate a counteracting autonomic response. Such autonomic response may be larger than the conscious response and may be followed by further autonomic responses directed toward restoring the original balance of the system. In addition, the individual may simultaneously exhibit an autonomic electrodermal response of many times such conscious response due to environmental effects such as the weather, temperature, atmospheric pressure, etc. Finally, a simultaneous subconscious electrodermal response through the central nervous system due to loud noises, personal psychological condition, etc., may occur which may either reinforce or counteract the conscious electrodermal response.

One object of this invention is to provide a reliable method and apparatus for utilizing "conscious" (i.e. "intentional" or "voluntary") electrodermal response and the like as a control means.

SUMMARY OF THE INVENTION

According to this invention, electrodermal response and the like of a biologic individual is utilized by programming an electrical device to respond in a desired humanly perceptible fashion to changes in the sense and amplitude of an electrical control signal only in a given range. A value characteristic of the state of an autonomic system, for example, the galvanic skin resistance of the individual, is then sensed and converted to an electrical signal, the absolute value of which changes in sense and amplitude with changes in the sensed value characteristic of the state of the autonomic system and such electrical signal is continuously adjusted in absolute value toward a given electrical value with a given time rate of change approaching the average time rate of change which can be achieved in the value characteristic of the state of the autonomic system by the central nervous system of a biologic individual. The resultant time rate of change in the absolute value of the electrical signal is converted to an electrical signal within the given range and used as the electrical control signal for the electrical device.

BRIEF DESCRIPTION OF THE DRAWING

This invention will be more fully understood from the following detailed description of the method when read in conjunction with the appended drawing showing a preferred embodiment of the apparatus wherein:

FIG. 1 is a perspective view of a stylized personal computer having a control means according to a preferred embodiment of this invention connected thereto.

FIG. 2 is a block diagram of the apparatus of FIG. 1.

FIG. 3 is a schematic diagram of a circuit for amplifying galvanic skin response and the like suitable for use in apparatus according to one embodiment of the teaching of this invention.

FIG. 4 is a graph of conventional resistance values at the GSR input of apparatus according to this invention plotted on the ordinate against time plotted on the abscissa.

FIG. 5 is a graph of the effective output resistance values of the apparatus corresponding to the input resistance values of FIG. 4 plotted on the ordinate against time on the abscissa.

FIG. 6 is a graph similar to FIG. 4 showing idealized GSR values for a first biologic individual in solid line and for a second biologic individual in broken line.

FIG. 7 is a graph similar to FIG. 5 but showing the position of an image on the face plate of a monitor in solid and broken lines corresponding to the resistance values of FIG. 6.

DETAILED DESCRIPTION OF THE INVENTION

Referring to the drawing an apparatus according to a preferred embodiment for practicing the method of this invention is shown. Thus, in FIG. 1, a conventional personal computer system 10 is shown as comprising a computer circuitry and keyboard unit 12 with a pair of disc or tape drives 13 and 14 and a cathode ray tube monitor 16 electrically connected thereto. Such system may be a personal computer system as manufactured and sold by the Apple, Atari, or Commodore computer manufacturing companies having a game paddle input port as is well known in the art. Such game paddles conventionally comprise simple variable resistors or potentiometers adapted to provide resistance values between about zero and about 150,000 ohms at the input port to the computer system. As is well known in the art, the circuitry 12 of the computer system may be programmed to respond to manual adjustment of the resistance value of the game paddle to produce a desired display on the cathode ray tube monitor 16. This is conventionally done by prerecording the program on a disc or tape which is then inserted into one of the disc or tape drives 13 and 14 to program the circuitry 12 of the computer system. Such prerecorded programs may comprise a game of some sort, for example, having a controllable element such as an image of a ball or other character which can be caused to move about on the face plate of the cathode ray tube monitor by manually changing the setting of the variable resistor or potentiometer of the game addle. Although a wide variety of mechanical elements for effecting the change in the resistance value of game paddles known in the prior art have been used, all of such game paddle devices comprise essentially a resistance element having a first wire connecting one end thereof to one input terminal of the game paddle input port, and a second wire connecting a movable tap on resistor to another input terminal of the game paddle input port.

According to the embodiment of this invention shown in the drawing, the conventional game paddle is replaced by a pair of wires electrically connected to a circuit including a pair of electrode members preferably having a coating of noble metal thereon. One of such electrode members may be considered connected to one input terminal of the game paddle input port and the other of such electrode members may be considered connected to the other input terminal of the game paddle input port. By placing the contact members in galvanic contact with the skin of a human individual, the skin resistance of such human individual may be considered to be imposed upon the game paddle input port to the computer system 10.

For example, as shown in FIG. 1, a device 20 comprising a body 21 of insulating material and a pair of close spaced metallic electrode members 22 and 23 mounted thereon is substituted for the game paddle. If the electrode members 22 and 23 are, in fact, directly electrically connected to the game paddle input port of the computer system 10 by means of a pair of wires 24 and 25 each connected to a different one of the electrode members 22 and 23, it has been found that certain individuals can simply place a first of their fingers on one of the electrode members 22 and a second of their fingers on the other electrode member 23 and successfully substitute voluntary variations in their galvanic skin resistance for manual changes in a game paddle in controlling a preprogrammed computer system 10. However, such control is undependable at best and impossible for many individuals.

The fact that the resistance value present between the electrodes 22 and 23 will vary in time, when such electrodes are in continuous galvanic contact with the skin of a human individual is known in the art as the galvanic skin response (GSR) or Psycho galvanic reflex (PGR) or electrodermal reflex (EDR). All of these terms refer to the phenomena involving changing electrical properties of the skin of a biologic individual including at least two distinct classes one of which is resistance present between two spaced points on the skin surface and the other of which is a potential difference between two spaced points on the skin surface. For the purposes of this invention, such phenomena will be referred to collectively as "electrodermal response".

Apparatus for measuring and recording electrodermal response accompanying emotional and other stresses of a subject have come into widespread use, particularly in connection with such response accompanying psychologically induced stresses in what has come to be popularly known as a "lie detector". Although much is known about electrodermal response, much information is still lacking as to variables affecting such response. For discussion of some of the problems reference is made to Chapter One of the book entitled "TECHNIQUES IN PSYCHOPHYSIOLOGY" edited by Irene Martin and Peter H. Venables, published by John Wiley and Sons in 1980. (See also the article titled "Skin Resistance and Galvanic Skin Response" published by Robert Edelberg et al in the Archives of General Psychiatry, Volume 7, September 1962, at pages 163 through 169 and an article titled "Problems in Measurement of Electrodermal Phenomena—Choice of Method and Phenomena—Potential, Impedance, Resistance" by T. W. Forbes, published in Psychophysiology, Volume 1, No. 1, July 1964, at pages 26 to 30.

In the prior art, electrodermal response although quick and transient, was known as a sensitive indicator of sympathetic activity level occurring in response to such influences as frightening stimuli or other emotional stress. The electrodermal response was believed to be involuntary in the sense that subjects could not suppress it readily, if at all, although it was recognized that a subject could voluntarily produce an electrodermal response by deep breathing or moving. Applicants have found that through the use of the proper method and apparatus it is possible to learn to control the electrodermal response with improved reliability and further, that voluntary electrodermal response can be utilized reliably and effectively as a control resistance at the game paddle input port of a computer, for example.

Thus, referring to FIG. 1 of the drawing, in order for an individual to play a game, for example, programmed into the computer system 10 under the control of electrodermal response the individual must first achieve a galvanic skin resistance within the range of a conventional game paddle which may be 0 to 150,000 ohms, for example. Although galvanic skin resistances less than 150,000 ohms may be exhibited by any individual under appropriate circumstances and may be achieved by certain individuals voluntarily and at any time, normal galvanic skin resistance is somewhat higher and in many individuals may remain at or above 200,000 ohms. In addition, the relative ability to change galvanic skin resistance varies widely between individuals. Certain individuals may be able to achieve wide variations in their galvanic skin resistance while others will only be able to effect relatively small changes in their galvanic skin resistance. Furthermore, the galvanic skin resistance of an individual will tend to "drift" rather than remain at and about a given level over an extended period of time.

If a particular individual can achieve a galvanic skin resistance less than 150,000 ohms so that it is within the range of an ordinary game paddle, then the computer can be programmed so that relatively small changes in galvanic skin resistance will produce the full range of control normally requiring tens of thousands of ohms variation. However, this requires that the individual not only be capable of causing a very large initial change in galvanic skin resistance but that the individual be capable of making very small voluntary changes in galvanic skin resistance of the order of a few ohms after the necessary value below 150,000 ohms is reached. It has been found that certain individuals can achieve such fine voluntary control. However, even those individuals are subject to involuntary drifting of their galvanic skin resistance by hundreds or thousands of ohms to values greater than 150,000 ohms due to external stimuli beyond their control.

According to this invention, the electrodes 22 and 23 are not directly connected to the input port of the computer 10. Instead, the device 20 includes a circuit 26 interposed between the electrodes 22, 23 and the wires 24, 25, respectively, as indicated by the block diagram in FIG. 2. As shown in FIG. 2, a third wire 27 is connected between the circuit 26 and the computer 10 in order to establish a common ground therebetween.

According to this invention, the circuit 26 senses the resistance present between electrodes 22, 23 and produces an electrical signal which changes in sense and amplitude directly with changes in the resistance sensed between the electrodes 22, 23. The circuit 26 includes means which continuously adjusts the absolute value of such electric signal toward a given electrical value with a given time rate of change. Finally, the cirtuit 26 includes means for converting the resultant electrical value to corresponding resistance value within the range of a conventional game paddle which may be 0 to 150,000 ohms, for example.

Thus, if the electrodes 22, 23 are not in contact with the skin of a biologic individual, the resistance therebetween will be very high, approaching infinity. The resulting electrical signal produced by the circuit 26 would tend to be very high but for the fact that the circuit 26 automatically adjusts such signal toward a given value. Such given value is then converted to a resistance value which is within the range of a conventional game paddle and preferably toward the middle of such range although it could be toward the upper or lower end of the range as desired. If a very low resistance is connected between the electrodes 22, 23, a correspondingly low electrical signal will be produced by the circuit 26 which will again be adjusted to the given value required to produce a resistance value within the range of a conventional game paddle. It will be understood that the resistance value produced in either case will be substantially the same value.

For ease of understanding, it may be assumed that the computer is programmed to produce a very simple game in which an image of a ball is presented on the faceplate of the cathode ray tube monitor 16 which image may be moved up and down on the faceplate of the monitor 16 by means of a conventional game paddle connected to the computer 10. For example, adjustment of the game paddle to its 0 resistance setting may move the image of the ball to the extreme bottom of the monitor 16 while adjustment of the game paddle to its maximum resistance setting will move the image of the ball to the extreme top of the monitor 16 with intermediate adjustments of the game paddle producing intermediate positions of the image of the ball. If the game paddle is then replaced by the circuit 26 and electrodes 22, 23 according to this invention with a low resistance connected between the electrodes 22, 23, the image of the ball will first move to the bottom of the faceplate of the monitor 16 and then upwardly until it reaches the preselected intermediate position. Similarly, if the low resistance is then removed from between the electrodes 22, 23, the image of the ball will move to the top of the faceplate of the monitor 16 and then return to the preselected intermediate position where it will remain so long as the very high resistance therebetween is unchanged.

If two adjacent fingers of the hand of a human individual are placed in contact with the electrodes 22 and 23, respectively, the image of the ball will first move to the bottom of the faceplate of the monitor 16 and then it will begin to move erratically between intermediate positions on the faceplate of the monitor 16. It has been found that the human individual by observing the faceplate of the monitor 16 can learn to cause the ball to move predominantly in one direction or the other or to remain stationary in a given position through appropriate voluntary control of the electrodermal response by the central nervous system.

At this point it should be noted that applicants' apparatus is not a "lie detector" or a "bio feedback" device as proposed in the prior art based on electrodermal response. This fact is due to a fundamental difference between applicants' method and apparatus and the teaching of the prior art. Thus, according to applicants' method and apparatus, the position of the image of the ball on the faceplate of the monitor 16 does not have any relationship to a particular general or overall psychological state of the human individual using the apparatus whereas it would be necessary for each position of the image on the faceplate of the monitor 16 to correspond to a particular general or overall psychological state of the human individual using the apparatus in order for it to operate as a "lie detector" or "bio feedback" device in accordance with the teaching of the prior art. This is due to the fact that applicant's apparatus is designed to continuously adjust the signal representative of the electrodemal response of the human individual using the apparatus toward a given value in order to enable the individual to accomplish an intended purpose (i.e., position the image of the ball at a particular place or cause it to move in a particular direction on the faceplate of the monitor 16.)

More particularly, "lie detector" devices and "bio feedback" devices of the prior art have included a manually adjustable control which was used to establish a given relationship between the operation of such devices and a particular psychological state of the subject. Changes in the psychological state of the subject from such given state are then monitored with information as to the given psychological state always being carefully maintained even though it was subsequently necessary to manually readjust the device in order to keep the electrodermal response within the range of the device. This is true even though certain of the prior art "lie detector" devices and "bio feedback" devices included means for automatically readjusting the device to keep the electrodermal response within the range of the device. By necessity, such readjustment had to be accomplished with a substantial time delay in order to avoid loss of information with respect to the given general or overall psychological state to which the response was to be related.

According to applicants' invention, the particular general or overall psychological state of the human individual using the apparatus is totally unimportant. Thus, no time delay is required in connection with the readjustment action according to applicant's invention. Instead, it is necessary that the time rate of the readjustment action approach the average time rate of change in electrodermal response that can be achieved by voluntary control through the central nervous system of the human individual using the apparatus. Thus, according to applicants' invention, a particular position of the image on the faceplate of the monitor 16 may be achieved in a multiplicity of psychological states thereby insuring that the human individual using the apparatus has continuous control over the position of the image on the faceplate.

Referring to FIG. 3 of the drawing, a preferred embodiment of the circuit 26 for use in accordance with the teaching of applicants' invention is shown. The circuit 26 includes a first operational amplifier 30 connected across the electrodes 22 and 23 to provide a constant current flow therebetween regardless of the resistance value present therebetween. The varying voltage thus present at the output of the first operational amplifier 30 is connected to the input of the second operational amplifier 32 through an RC network 34. The second operational amplifier 32 amplifies the voltage present at the input thereof. The time constant of the RC network 34 is selected to provide a time rate of change which approaches the average time rate of change in electrodermal response which may be attained by the central nervous system under the conscious control of the subject.

The circuit 26 as shown in FIG. 3 is specifically adapted for connection to the game paddle input port of a computer as currently manufactured by the Apple Computer Company under the type designation "Apple II". In such a computer a five volt power supply with respect to the computer ground is available for connection to one end of the variable resistor of the game paddle through the wire 24 with the other end of the variable resistor connected to the computer ground through the wire 27 and the adjustable tap of the variable resistor connected to the input port through the wire 25.

In the circuit 26 according to the embodiment of the invention shown in FIG. 3, all of the points labeled A are connected to the five volt power supply through the wire 24, all of the points labeled C are connected to the computer ground through the wire 27 and the point labeled B is connected to the game paddle input port through the wire 25. As shown at the left side of FIG. 3, a first transistor circuit 36 is connected between the five volt power supply and computer ground through the wires 24 and 27, respectively. As shown at the right of FIG. 3, a second transistor circuit 38 is connected between the five volt power supply and the game paddle input port through the wires 24 and 25, respectively.

Thus the first transistor circuit comprises a transistor 40 having its collector 41 connected to the five volt power supply and its emitter 42 connected through a resistor 43 to computer ground. A capacitor 44 is connected in parallel with a pair of series connected resistors 45 and 46 between the collector 41 and emitter 42 of the transistor 40. The base 47 of the transistor 40 is connected to the junction 48 between the resistors 45 and 46. The first transistor circuit 36 functions to provide a constant reference voltage of about two and one-half volts at the output 49 thereof and to smooth out any voltage fluctuations which may be present in the voltage supplied by the computer 10. The reference voltage output 49 of the transistor circuit 36 is taken between the emitter 42 of the transistor 40 and the resistor 43 and is connected directly to one input 51 of the operational amplifier 30.

One of the electrodes 22 is directly connected to the other input 52 of the operational amplifier 30. The other electrode 23 is directly connected to the output 53 of the operational amplifier 30. A resistor 54 of large resistance value is connected between the electrode 22 and computer ground thus limiting the current flow between the electrodes 22 and 23 to a very low value in order to reduce toward minimum any possibility that such current flow might stimulate or otherwise affect the autonomic system or central nervous system of the subject whose electrodermal response is to be utilized.

Thus the operational amplifier 30 will cause a given small current flow through the galvanic skin resistance of a subject in contact with the electrodes 22 and 23 regardless of the value of such skin resistance. The voltage at the output 53 of the operational amplifier 30 will fluctuate as required to maintain the given small current flow between the electrodes 22 and 23 regardless of variations in the galvanic skin resistance present between the electrodes 22 and 23.

A capacitor 56 is connected across the electrodes 22 and 23 and a capacitor 58 is connected between the output 53 of the operational amplifier 30 and computer ground. The capacitors 56 and 58 function to filter out noise and spurious responses which may be present between the output of operational amplifier 30 and computer ground 27.

The voltage present at the output 53 of the operational amplifier 30 is coupled to the operational amplifier 32 through the RC network 34. The RC network 34 comprises a capacitor 60 having one terminal connected to the output 53 of the operational amplifier 30. The other terminal of the capacitor 60 is connected to the input 51 of the operational amplifier 30 through the series connected resistors 62 and 64. The junction between the series connected resistors 62 and 64 is connected through a resistor 66 to the adjustable center tap 67 of a potentiometer 68. The potentiometer 68 has its opposite ends connected to the five volt power supply and computer ground through the wires 24 and 27, respectively.

The other terminal of the capacitor 60 is also directly connected to one input 71 of the operational amplifier 32. The other input 72 of operational amplifier 32 is connected to the output 73 thereof through a resistor 74 and to the reference voltage at 49 through a resistor 75. A capacitor 76 is connected in parallel with the resistor 74. The output 73 of the operational amplifier 32 is connected through a resistor 78 to the second transistor circuit 38.

The second transistor circuit 38 comprises a transistor 80 having its collector 81 connected to the game paddle input port through wire 25. The emitter 82 of the transistor 80 is connected to the five volt power supply through a resistor 84. The base 86 of the transistor is connected both to the five volt power supply through a resistor 88 and to the output 73 of the second operational amplifier 32 through the resistor 78. The function of the second transistor circuit 38 is to present a variable resistance value at the game paddle input port of the computer 10 which simulates the variable resistor of a conventional game paddle. Thus the voltage applied to the base 86 of the transistor 80 of the transistor circuit 38 will determine the value of the effective resistance presented by the transistor circuit 38 to the game paddle input port of the computer 10.

The RC network 34 in combination with the operational amplifier 32 functions as a slope detector with respect to changes in the resistance present between the electrodes 22 and 23. In other words, the RC network 34 and operational amplifier 32 with its associated circuitry apply a voltage to the base 86 of transistor 80 which is representative of the time rate of change in the resistance value present between the electrodes 22 and 23 as will be more fully described hereinafter. It will be understood that if the resistance value between the electrodes 22 and 23 is constant, no signal will be coupled through the capacitor 60 to the input 71 of the operational amplifier 32. In such condition, the center tap 67 of the variable resistor 68 is adjusted to provide a voltage which when amplified by the operational amplifier 32 and applied to the base 86 of the transistor 80 through the resistor 78 will cause the transistor circuit 80 to produce an effective resistance value within the range of a conventional game paddle. For example, the transistor 80 and resistors 84, 88 may be selected so that an appropriate adjustment of the center tap 67 will produce a given resistance value between the five volt power supply at wire 24 and the game paddle input port at wire 25 which is located at or about the middle of the range of a conventional game paddle. Changes in the electrical resistance value present between the electrodes 22 and 23 will then produce changes in the effective resistance value present between the five volt power supply and the game paddle input port as more fully described with reference to FIGS. 4 through 7.

In an embodiment of this invention as actually constructed and successfully operated, the electrical and electronic components of the circuit 26 as shown in FIG. 3 of the drawing were as follows:

| Operational amplifier 30 | National LM 358 |
| --- | --- |
| Operational amplifier 32 | Dual Op-amp. |
| Transistor 40 | Motorola 2N4400 |
| Resistor 43 | I.R.C. 1.5K ohm |
| Capacitor 44 | Mallory 4.7 MFD |
| Resistor 45 | I.R.C. 10K ohm |
| Resistor 46 | I.R.C. 19K ohm |
| Resistor 54 | I.R.C. 3.3 MEG. |
| Capacitor 56 | Mallory 4.7 MFD |
| Capacitor 58 | Mallory .1 MFD |
| Capacitor 60 | Sprague 100 MFD |
| Resistor 62 | I.R.C. 4.7K ohm |
| Resistor 64 | I.R.C. 220 ohm |
| Resistor 66 | I.R.C. 220K ohm |
| Potentiometer 68 | I.R.C. 100K ohm |
| Resistor 74 | I.R.C. 1 MEG ohm |
| Resistor 75 | I.R.C. 560 ohm |
| Capacitor 76 | Mallory .1 MFD |
| Resistor 78 | I.R.C. 100K ohm |
| Transistor 80 | Motorola 2N 4402 |
| Resistor 84 | I.R.C. 1.5K ohm |
| Resistor 88 | I.R.C. 51K ohm |

Referring to FIGS. 4 and 5 of the drawing, a pair of corresponding conceptual graphs of resistance values plotted on the ordinate with respect to time plotted on the abscissa are shown. Thus the graph of FIG. 4 represents a resistance value changing in time between the electrodes 22 and 23. The graph of FIG. 5 represents the resulting changing effective resistance of the transistor circuit 38 at corresponding points in time according to this invention.

It is emphasized that according to the teaching of this invention, the base line resistance value shown in FIG. 4 has no significance whatever other than to aid in the understanding of the following description and may be hundreds of thousands of ohms. No matter what the absolute value of such base line is, so long as it remains constant, the resulting resistance value of the transistor circuit 38 will be a value at or about the middle of the resistance range of a conventional game paddle as represented by the base line in FIG. 5.

If the resistance present between the electrodes 22 and 23 increases as represented by the graph segment 91 of FIG. 4, a resulting increase in the given resistance value of the transistor circuit 38 will occur as represented by the graph segment 101 in FIG. 5. According to this invention, the slope of the segment 91 of FIG. 4 will determine the height reached by the segment 101 above the base line of FIG. 5. If the resistance present between the electrodes 22 and 23 then decreases as represented by the graph segment 92 of FIG. 4, the resistance value of the transistor circuit 38 will decrease as shown by the graph segment 102 in FIG. 5. As shown by the graph segment 102, the decrease in resistance value of the transistor circuit 38 will initially have a slope greater than the slope of the segment 92 and again, the amount by which the effective resistance of the transistor circuit 38 decreases below the base line of FIG. 5 will be directly proportional to the slope of the graph segment 92 of FIG. 4. If the resistance value between the electrodes 22 and 23 then remains constant for a period of time as represented by the graph segment 93 of FIG. 4, the effective resistance value of the transistor circuit 38 will return to the given resistance value of the base line of FIG. 5 as indicated by the graph segment 103.

If the resistance value present between the electrodes 22 and 23 then increases at a high slope as represented by the graph segment 94 in FIG. 4, the effective resistance value of the transistor circuit will increase rapidly to a higher value representative of the higher slope of the graph segment 94 as indicated by the graph segment 104 of FIG. 5. Again, if the resistance value present between the electrodes 22 and 23 remains constant as indicated by the graph segment 93' of FIG. 4, the effective value of the transistor circuit 38 will decrease toward the given base line value as shown by the graph segment 103' of FIG. 5.

If the resistance value between the electrodes 22 and 23 again increases as shown by the graph segment 91' with a slope identical to the graph segment 91, the resultant effective resistance of the transistor circuit 38 represented by the graph segment 101' in FIG. 5, will approach a value identical to that represented by the graph segment 101 of FIG. 5.

More importantly, if the resistance value present between the electrodes 22 and 23 changes with a given slope over an extended period of time as represented by the graph segment 95 in FIG. 4, the effective resistance value of the transistor circuit 38 will attain a given constant value as represented by the graph segment 105 in FIG. 5. As represented by the graph segment 93" of FIG. 4, if the resistance value present between the electrodes 22 and 23 attains a given value and then remains constant, the effective resistance value of the transistor circuit 38 will tend to return to its given base value as represented by the graph segment 103" of FIG. 5.

Graph segments 96, 91" and 97 of FIG. 4 considered in conjunction with graph segments 106, 101" and 107 of FIG. 5 illustrate that if the resistance value present between the electrodes 22 and 23 increases with a given slope and then such slope decreases, the effective resistance value of the transistor circuit 38 will first increase to a high value corresponding to the initial slope and then decrease to a lower values corresponding to the decreasing slopes.

Graph segments 98 and 99 of FIG. 4 in conjunction with graph segments 108 and 109 of FIG. 5 illustrate that an exponential increase or decrease in the resistance present between the electrodes 22 and 23 will result in a modified exponential increase or decrease in the resistance value of the transistor circuit 38.

It is pointed out that the graph shown in FIG. 5 is an idealized approximation intended to illustrate the effects of the time constant of the RC network 34. In the circuit 26 according to the embodiment of this invention shown in FIG. 3, the RC network 34 has a time constant slightly less than one-half second. Such time constant approaches the average reaction time of the human central nervous system to visual stimuli where discrimination between more than two qualities is required. Thus, referring to graph segment 93''' in FIG. 4 and corresponding graph segment 103''' in FIG. 5, the time rate of change at which a given absolute value present between the electrodes 22 and 23 is accommodated to tend to provide an effective resistance value for the transistor circuit 38 corresponding to the base line value shown in FIG. 5 approaches the average time rate of change which can be made in the resistance value present between the electrodes 22, 23 by the central nervous system of an individual.

Referring to FIG. 6, a graph representing the galvanic skin resistance of a first individual imposed upon the electrodes 22 and 23 plotted on the ordinate against time on the abscissa is represented by the solid line 110. Similarly, a graph of the galvanic skin resistance of a second individual plotted on the ordinate against time on the abscissa is represented by the broken line 120.

Referring to FIG. 7, the position of an image on the face plate of the cathode ray tube monitor 16 of the computer 10 according to this invention is plotted on the ordinate against time on the abscissa. The solid line 130 represents the position of the image in response to the galvanic skin resistance of the first individual shown by the solid line 110 in FIG. 6 and the broken line 140 in FIG. 7 represents the position of the image in response to the galvanic skin resistance of the second individual represented by the broken line 120 in FIG. 6. Thus referring to the extreme left hand side of FIGS. 6 and 7, it will be understood that according to the teaching of this invention as described hereinabove, if the galvanic skin resistance of the two individuals remains constant for a period of time, the image on the face plate will be substantially centered regardless of the relative absolute values of their galvanic skin resistance. When the galvanic skin resistance of the first individual increases with a given slope as indicated by the graph segment 111 in FIG. 6, the image on the face plate will move upwardly to a given position where it will remain as indicated by the graph segment 131 in FIG. 7 so long as the given slope is maintained. If the slope is increased as indicated by the graph segment 112, the image on the face plate will move upwardly to a new position as indicated by the graph segment 132 in FIG. 7 where it will remain until the slope again changes as indicated by the graph segment 113 in FIG. 6 at which time it will move to a new position as indicated by the graph segment 133 in FIG. 7.

Graph segments 114 and 115 in FIG. 6 illustrate further increases in the galvanic skin resistance of the first subject at different slopes until a fairly high galvanic skin resistance is attained as indicated by the graph segment 116. Similarly, graph segments 134 and 135 illustrate the position of the image on the face plate corresponding to the slopes of the segments 114 and 115. The graph segment 136 in FIG. 7 in conjunction with the graph segment 116 of FIG. 6 illustrates that the image will tend to return to center when the galvanic skin resistance of the first individual remains constant even though it is now at a much higher absolute value.

Graph segments 121 through 126 of the graph 120 in FIG. 6 are mirror images of graph segments 111 through 116 of graph 110. Similarly, graph segments 141 through 146 of FIG. 7 are mirror images of graph segments 131 through 136.

It will be seen that although there is a wide difference between the absolute values of the galvanic skin resistance of the first individual as represented by graph segment 116 and the galvanic skin resistance of the second individual as represented by the graph segment 126, the image on the face plate of the cathode ray tube monitor will nevertheless tend to return to about the middle of the face plate. Furthermore, it will be seen that the first and second individuals can achieve identical control of the image in spite of the wide disparity between their galvanic skin resistances. In other words, it will be seen that, since graph segments 117 and 118 have the same slope as graph segments 127 and 128 in FIG. 6, the resultant position of the image on the face plate will be identical as indicated by graph segments 137 and 147, 138 and 148 of FIG. 7. Thus, if the first and second individuals have the same intention, they can achieve the same position of the image on the face plate regardless of the state of their respective galvanic skin resistances.

Alternatively, graphs 110 and 120 may represent the galvanic skin resistance of the same individual at two different times. First when the individual's autonomic system is causing his galvanic skin resistance to increase over a period of time as represented by graph 110. Graph 120 would indicate that at a different time, the individual's autonomic system was causing a decrease in the galvanic skin resistance of the individual.

According to this invention, it has been found that individuals can modify the slope of an increase or decrease in galvanic skin resistance at will, thereby enabling the individual to control the position of an image on the face plate of the cathode ray tube monitor reliably and with repeatable certainty. The same signal which controls the position of the image on the face plate of the cathode ray tube monitor 16 can be used to control the position of other instrumentalities such as robots or robotic devices, for example.

It is pointed out that the changes in the effective resistance of the transistor circuit 38 according to this invention need not extend throughout the full range of a conventional game paddle. Instead, appropriate programming of the computer 10 can be used to amplify much smaller changes in the resistance value to enable the full range of control of the position of the image on the face plate of the cathode ray tube monitor. In this regard, it is noted that the resistor 74 may be selected to provide a desired gain in the operational amplifier 32 and thus the range of variation in the effective resistance of the transistor circuit 38. In the embodiment of this invention shown in the drawing, a gain of about 2000 has been found to be preferable. A higher gain will make the circuit so sensitive that even the heartbeat of the individual can be detected. Lower gains tend to require excessive concentration on the part of the individual in order to effect a time rate of change in galvanic skin resistance sufficient to produce the desired positioning of the image on the face plate.

It is believed that those skilled in the art will make obvious modifications in the specific circuit 26 as shown in the drawing and specifically described hereinabove without departing from the scope of applicants' method and apparatus as taught above and claimed in the following claims.

What is claimed is:

1. The method of utilizing electrodermal response or other autonomic nervous system functions of a biological individual as a conscious and intentional control means, comprising the steps of:
   a) programming an electrical device to respond in a desired humanly perceptible fashion to changes in the sense and amplitude of an electrical control signal only in a given range within which the electrical device is capable of response;
   b) sensing a value characteristic of the state of said electrodermal response or other autonomic nervous system function of the individual;
   c) converting said sensed value into an electrical signal which changes in sense and amplitude with changes in said sensed value;
   d) continuously adjusting said electrical signal toward a given electrical value which represents a zero rate of change of the sensed value, with a range of velocities of adjustment approaching the average range of velocities of adjustment which can be achieved by the central nervous system of said biologic individual in said value characteristic of the state of said electrodermal response or other autonomic nervous system function;
   e) deriving a representation of said adjustment of the electrical signal and converting it to an electrical output signal having a value corresponding to a zero rate of change of the sensed value at about the middle of said given range and which varies directly in sense and amplitude with changes in said representation, with a difference between the minimum and maximum values thereof that is a substantial portion of said given range;
   f) utilizing said electrical output signal as said electrical control signal by inputting the electrical output signal to said electrical device, and
   g) through the biologic individual, consciously making inputs to the central nervous system in order to affect the autonomic nervous system to induce changes to said value characteristic in a positive or negative direction and thereby inducing a response in the electrical device in a positive or negative direction.

2. Apparatus utilizing electrodermal response or other autonomic nervous system functions of a biologic individual as a conscious control means, comprising in combination:
   a) an electrical device programmed to respond in a desired humanly perceptible fashion to changes in the sense and amplitude of an electrical control signal only in a given range at the input thereto, said given range being a range within which the electrical device is capable of response;
   b) means for sensing a value characteristic of the state of said electrodermal response or other autonomic nervous system function;
   c) means for converting said sensed value into an electrical signal which changes in sense and amplitude with changes in said sensed value;
   d) means for continuously adjusting said electrical signal toward a given electrical value which represents a zero rate of change of the sensed value, with a range of velocities of adjustment approaching the average range of velocities of adjustment which can be achieved by the central nervous system of said biologic individual in said value characteristic of the state of said electrodermal response or other autonomic nervous system function;
   e) means for deriving a representation of said adjustment of the electrical signal and converting it to an electrical output signal having a value corresponding to a zero rate of change of the sensed value at about the middle of said given range and which varies directly in sense and amplitude with changes in said representation, with a difference between the minimum and maximum values thereof that is a substantial portion of said given range; and
   f) means coupling said electrical output signal to said input of said electrical device to provide said electrical control signal thereto;
   g) whereby the biologic individual consciously makes inputs to the central nervous system in order to affect the autonomic nervous system to induce changes to said value characteristic in a positive or negative direction and thereby inducing a response in the electrical device in a positive or negative direction.

3. The apparatus of claim 2, wherein the means for continuously adjusting the electrical signal includes an RC (resistance-capacitance) network receiving said electrical signal.

4. The apparatus of claim 3, wherein the RC network has a time constant of about one-half second.

5. The apparatus of claim 2, wherein the electrical device comprises a computer pre-programmed to perform selected operations in response to signals in a given range applied to an input means of the computer, and wherein
   the apparatus includes a sensor means for sensing a time varying absolute value representative of the state of the autonomic nervous system of the individual,
   the means for sensing a value characteristic and the means for converting the sensed value include first circuit means having an input and an output with the input thereof connected to the sensor means, said first circuit means having means for producing a time varying electrical signal corresponding to said sensed time varying absolute value of the autonomic nervous system,
   the means for continuously adjusting said electrical signal includes second circuit means having an input and an output, with the input thereof connected to the output of the first circuit means, said means for continuously adjusting further including means for producing a composite time varying electrical signal at the output of the second circuit means, representing the continuous adjustment of the electrical signal,
   the means for deriving a representation of said adjustment including third circuit means having an input and an output, with the input thereof connected to the output of the second circuit means, said third circuit having means for converting the composite time varying electrical signal at the output of the second circuit means to said signals in said given range, and the means coupling said electrical output signal includes means connecting the output of the third circuit means to said input means of said computer.

6. The apparatus of claim 2, wherein said electrical device has an input, the means for sensing a value characteristic includes a pair of electrodes with means for connection to the individual at spaced locations, and with means for establishing a constant electrical current flow between the electrodes, the means for converting said sensed value includes an operational amplifier having two inputs and an output, the means for continuously adjusting said electrical signal includes means connecting one of said electrodes to one input of the operational amplifier through the capacitor of a resistance-capacitance network having an RC (resistance-capacitance) time constant of about one-half second, the means for deriving a representation of said adjustment includes resistor means connecting the output of the operational amplifier to the other input thereof to establish a given gain through the operational amplifier, and the means coupling said electrical output signal to said input of said electrical device includes means for converting the output of the operational amplifier to an electrical control signal in said given range and for applying said control signal to the input of said electrical device.

* * * * *